United States Patent [19]

Golub

[11] Patent Number: 4,973,251

[45] Date of Patent: Nov. 27, 1990

[54] MEANS AND METHODS FOR DENTAL RESTORATION

[76] Inventor: Jeff E. Golub, 128 E. 71st St., New York, N.Y. 10021

[21] Appl. No.: 388,511

[22] Filed: Aug. 2, 1989

[51] Int. Cl.$^5$ .............................................. A61C 5/00
[52] U.S. Cl. ..................................... 433/215; 433/26; 433/217.1; 433/229
[58] Field of Search ...................... 433/26, 217.1, 215, 433/229; 446/26, 27; 272/8 N

[56] References Cited

U.S. PATENT DOCUMENTS

| | | | |
|---|---|---|---|
| 1,712,043 | 5/1929 | Limbarth | 433/215 |
| 2,169,719 | 8/1939 | Bush | 433/26 |
| 2,341,153 | 2/1944 | Myerson | 433/26 |
| 4,306,860 | 12/1981 | Janssen et al. | 433/26 |
| 4,534,961 | 8/1985 | Liff | 424/63 |
| 4,747,776 | 5/1988 | Sudderth | 433/26 |

OTHER PUBLICATIONS

"Novelties" Catalog, Johnson, Smith and Co., of Detroit, 1947, p. 321, Make up supplies-Black Wax.

*Primary Examiner*—John J. Wilson
*Attorney, Agent, or Firm*—James P. Malone

[57] ABSTRACT

A process of applying a temporary diagnostic, consultative restoration to teeth to demonstrate to the patient how the restoration will look after it is finished, comprising the steps of, applying color to the wax cover, which may include sticks, ropes or cakes of wax, applying a wax cover to the teeth, carving the wax to the desired shape, applying a petroleum or acrylic cover to the wax to create a shine like real teeth. The material includes a predetermined amount of soft wax of predetermined color to cover one or more teeth, applied to the teeth, and a petroleum or acrylic base cover applied to the wax to make the restoration shine like natural teeth.

5 Claims, No Drawings

MEANS AND METHODS FOR DENTAL RESTORATION

This invention relates to cosmetic dental restoration and more particularly, to means and methods for applying a temporary diagnostic, consultative restoration to teeth to demonstrate to the patient how the restoration will look after it is finished.

BACKGROUND

Cosmetic restoration is needed to improve the appearance of teeth. Therefore, it is important and necessary to show the patient what the final appearance of the teeth will be. The present invention solves this problem as will be explained.

When the patient has approved a temporary restoration, photographs may be taken so that the cosmetic dentist will be able to duplicate the approved restoration in permanent form.

PRIOR ART

No prior art is known.

THE INVENTION

A process of applying a temporary diagnostic, consultative restoration to the teeth to demonstrate to the patient how the restoration will look after it is finished, comprising the steps of:
 selecting wax of matching color,
 applying the colored wax cover to the teeth, carving the wax to the desired shape,
 applying a petroleum or acrylic cover to the wax to create a shine like real teeth, and means for applying a temporary diagnostic, consultative restoration to teeth, comprising a predetermined amount of soft wax of predetermined color, to cover one or more teeth, and a petroleum or acrylic base cover applied to the wax to make the restoration shine like natural teeth.

OBJECTS OF THE INVENTION

A principal object of the invention is to provide a new and improved temporary diagnostic, consultative restoration to teeth to demonstrate to the patient how the restoration will look after it is finished.

Another object of the invention is to provide means for applying a temporary diagnostic, consultative restoration to teeth.

These and other objects of the invention will be apparent from the following specification.

The method of applying a temporary, diagnostic consultative restoration to teeth to demonstrate to the patient how the restoration will look after it is finished, comprises the steps of applying a colored wax cover to the teeth, carving the wax to the desired shape, applying a petroleum cover to the wax to create a shine like real teeth.

The means for applying the temporary diagnostic, consultative restoration comprise a predetermined amount of soft wax of predetermined color, to cover one or more teeth, and a petroleum base or acrylic cover to be applied to the wax to make the restoration shine like natural teeth.

The present invention is useful not only for creating a pleasing cosmetic appearance but may also be used for theatrical purposes, for instance, in horror movies where sinister and deformed teeth can be applied to an actor or an animal, the mock up restoration will demonstrate to the actor, director and costume designer, how the mock up insert might look.

The wax colors include pink for indicating gum line, and black for visually showing shortened teeth.

It is claimed:

1. Process of applying a temporary diagnostic, consultative restoration to teeth to demonstrate to the patient how the restoration will look after it is finished, comprising the steps of:
 applying color to the wax to approximate tooth color, plus pink for gums, and black to visually shorten teeth,
 applying a wax cover to the teeth,
 carving the wax to the desired shape,
 applying a petroleum cover to the wax to create a shine like real teeth.

2. The process as in claim 1, comprising the step of applying pink color to demonstrate a favorable gum line.

3. Means for applying a temporary diagnostic consultative restoration to teeth, comprising:
 soft wax of predetermined color to cover one or more teeth,
 a petroleum base or acrylic base cover applied to the wax to make the restoration shine like natural teeth.

4. Apparatus as in claim 3, wherein the color material includes black color applied to the ends of the teeth to visually shorten the teeth.

5. Apparatus as in claim 3, wherein the color material includes pink color applied to the teeth, to create a favorable gum line.

* * * * *